United States Patent [19]

Vaughan

[11] Patent Number: 4,699,344
[45] Date of Patent: Oct. 13, 1987

[54] SUPPORT ASSEMBLY

[76] Inventor: Thomas L. Vaughan, 27272 Cool Water Ranch Rd., Valley Center, Calif. 92082

[21] Appl. No.: 793,964

[22] Filed: Nov. 1, 1985

[51] Int. Cl.$^4$ .................................................. F16M 11/38
[52] U.S. Cl. ........................................ 248/170; 248/167; 248/188.7; 267/159; 403/95
[58] Field of Search .............. 248/170, 171, 168, 167, 248/188, 188.7, 528; 403/95; 108/1, 12; 135/67; 267/41, 15 R, 159

[56] References Cited

U.S. PATENT DOCUMENTS

| | | | |
|---|---|---|---|
| 1,863,756 | 6/1932 | Lufkin | 248/170 |
| 3,921,947 | 11/1975 | Adam | 248/168 X |
| 4,010,922 | 3/1977 | Heller et al. | 248/170 X |
| 4,061,302 | 12/1977 | Boone | 248/170 |
| 4,074,881 | 2/1978 | Bickford | 248/170 X |
| 4,262,871 | 4/1981 | Kolk et al. | 248/188.7 |
| 4,332,378 | 1/1982 | Pryor | 248/188.7 X |
| 4,548,379 | 10/1985 | Seely et al. | 248/170 X |

Primary Examiner—Ramon O. Ramirez
Attorney, Agent, or Firm—Knobbe, Martens, Olson & Bear

[57] ABSTRACT

Applicant's novel invention comprises an easy to use, portable, and versatile base support assembly attachable to a wide variety of equipment poles. The versatility of the support assembly is provided by a thick resilient sleeve with an internal diameter sufficient to mate with the ends of equipment poles of varying diameters. The outer surface of the resilient sleeve is mateable with an axial bore formed in the central hub of the assembly. Thereby, many different diameters of equipment poles may be accommodated by the system. Upright stability of the pole is achieved by means of an additional bolt set within the central hub, mating with a suitable threaded bore in the equipment pole. Applicant's invention has legs that fold in order to enhance portability of the base support. These legs are biased toward the folded storage position for ease of operation. To maintain the legs in an operational position, biased, pivotally-mounted latches are provided, having a hook portion that engages a collar extending from the central hub. To make it easy for the user to move the leg to a locking position, the hook portion may be beveled so as to contact and then slide over the collar during rotation, after which the hook portion falls over and lockably engages the collar.

19 Claims, 2 Drawing Figures

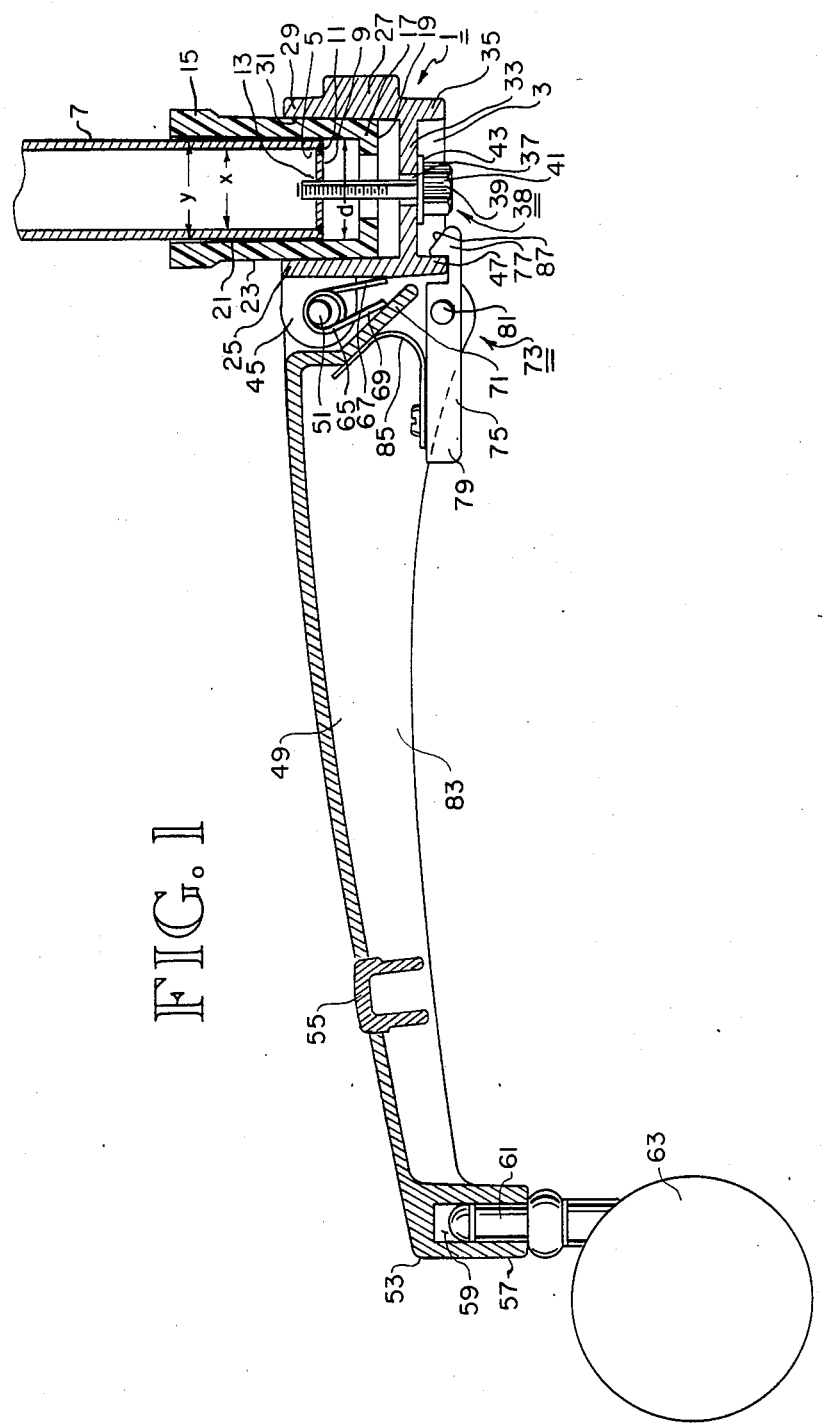

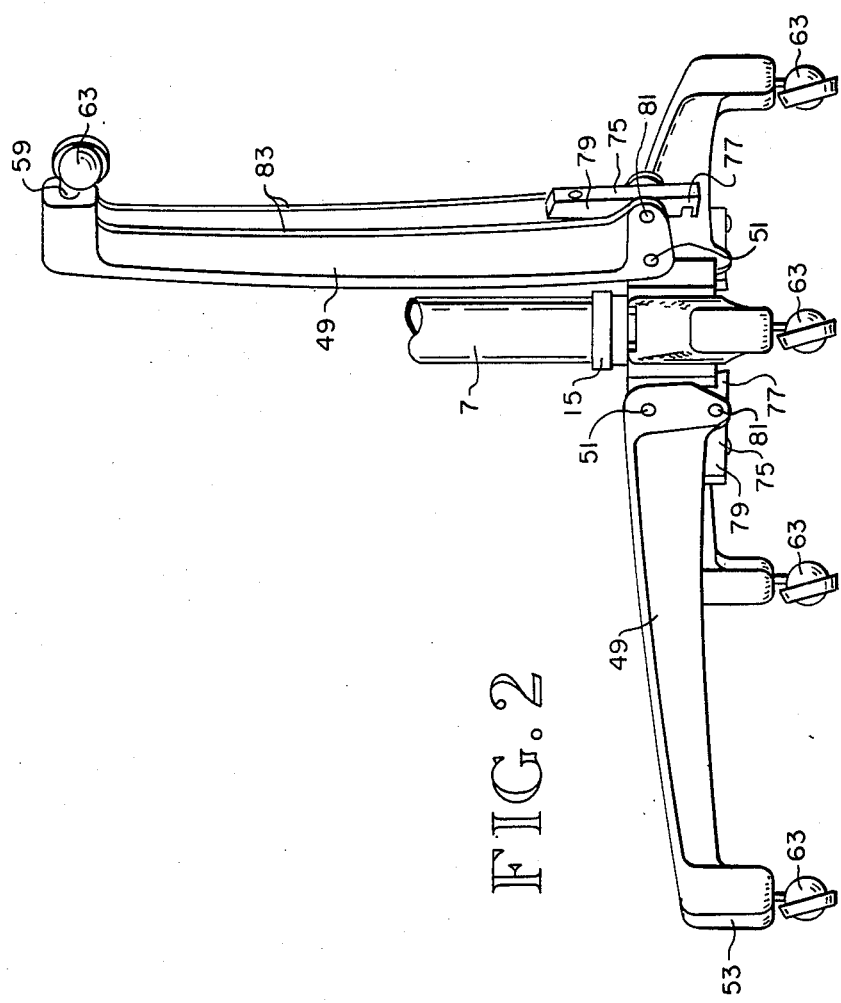

4,699,344

SUPPORT ASSEMBLY

BACKGROUND OF THE INVENTION

1. Field of the Invention

This invention pertains to the field of medical care products. More particularly, it pertains to the area of medical hardware and specifically, a support assembly for an upright pole that itself may support various medical devices such as intravenous bags, blood monitors, nurse notification devices and blood pressure equipment.

2. Description of the Prior Art

Inpatient medical care has traditionally been confined to the hospital. Hospitals have large storage areas and thus there was no need for medical hardware to be collapsible and it was stored in its fully extended geometry. All that has since changed. With higher hospital care costs, hospital fixed expenses have been forced to be minimized and storage area has been converted to bed space. This requires hospital hardware to be stored in smaller spaces and extreme hardship has been encountered in that fully extended hardware is not only difficult to store in a confined area but substantial damage is caused to the hardware under these conditions.

In addition, there has been a surge in the development of small, economic treatment facilities in an effort to minimize fixed expenses. These small treatment facilities have little storage area and the hardware is required to be capable of confined storage.

Further, the median age of the United States population is on the increase. This has resulted in more elderly people and concomitantly, a greater need for medical care. The government has been instrumental in attempting to decrease hospital and medical care coverage and this has resulted in private efforts to conduct medical treatment in the home. Home treatment necessitates the transport of medical hardware via automobile and, these factors have urged the development of collapsible medical hardware.

SUMMARY OF THE INVENTION

This invention comprises a support assembly for an upright support hardware pole that is foldable to a small configuration for ease in transport and storage. The traditional enlarged and heavy pole base has been changed to a series of radial legs to provide full support to whatever is being supported on the pole and, in addition, permits the legs to be folded up around the pole for ease in transportation, packaging and storing. The general enlarged base of approximately two square feet has been, by virtue of this invention, reduced to a matter of a few square inches thus allowing the visiting nurse to easily load and transport a plurality of these devices in a passenger vehicle where such would not be the case with the traditional fully extended pole base.

This invention comprises a base that is retrofittable on the bottom of a wide variety of support poles and, in addition, provides for a cushioning sleeve to be interposed the support pole and the legs to take up the shock of loading and unloading the pole with heavy medical equipment thus providing more stability to this inventive device than is traditionally found in the fully extended, circular base. The legs of the support assembly of this invention are adapted to provide strong support for heavy loads placed on the support pole and, when the pole is unloaded, to be easily and quickly pivoted upward into parallel arrangement with the pole to reduce the overall geometry of the base to a few square inches.

Accordingly, the main object of this invention is a support assembly for a upright medical equipment support pole that is foldable to a small geometry for ease in storing and transportation. Other objects include a support assembly that provides cushioning and shock absorbency for support poles that are loaded and unloaded with heavy equipment; a support assembly that is easily, quickly and conveniently foldable to a storage configuration and unfoldable into a working configuration by merely tripping a locking hook pivotally attached to each support leg; a support assembly that is retrofittable to virtually every support pole in existence and a support assembly that provides for receipt on the support leg ends of a variety of roller casters that permit travel on the loaded pole over a variety of surfaces including rugs, carpeting and flat surfaces.

These and other objects of the invention will become more apparent upon a close reading of the Description of the Preferred Embodiment taken together with the drawings attached thereto. While only one or two embodiments of the assembly will be described and shown, other equivalent constructions are fully contemplated within the spirit and scope of this invention.

DESCRIPTION OF THE DRAWINGS

FIG. 1 is a cross-sectional view of the inventive support assembly and a lower portion of a typical medical support pole attached thereto showing one of the legs in its support position.

FIG. 2 shows a side plane view of one embodiment of the support assembly of this invention and shows one of the legs in its folded, storage position.

DESCRIPTION OF THE PREFERRED EMBODIMENT

FIG. 1 shows base attachment means 1 for connecting a support assembly generally shown at 3 to the bottom end 5 of a typical hollow aluminum or stainless steel hardware support pole 7. Base attachment means 1 shows a metal or other hard washer 9 having a circular outside shape of a diameter "d" at least equal to the inside diameter "x" of support pole 7 and is attached to pole bottom end 5 by various means such as a weldment shown generally at 11 or some other rigid attachment such as glue, threading etc. Washer 9 contains a centrally located threaded bore 13 formed therethrough.

A generally cylindrical cushion sleeve 15 is positioned over base attachment means 1 having a lower end 17 comprising an inwardly turned end portion 19 for abutment against bottom pole end 5. Sleeve 15 further includes a pair of concentric inner and outer tapered surfaces 21 and 23 preferrably mutually concentric extending therealong. Sleeve 15 is made of a softer material, such as glass fiber-filled molded polymeric material, to provide for shock absorbency of loads placed upon pole 7 and this inventive support assembly. Inner tapered sleeve surface 21 has a least diameter, at the narrowest part of said inner tapered surface, that is less than the outside diameter "y" of pole 7 and has a greatest diameter that is greater than said outside pole diameter "y". This allows sleeve 15 to be positioned over poles of slightly varying outside diameter that is commonly experienced in the trade.

A spider 25, including a center hub 27, having an upwardly opening collar 29 that includes an inverted conical frustum surface 31 adapted to receive therein is positioned over cushion sleeve 15. A cross-web 33 closes the lower end 35 of collar 29 except for a central aperture 37 formed therein that permits passage from below of retaining means 38, such as a headed bolt 39 upward through inwardly turned sleeve end portion 19 and into threaded bore 13 in washer 9. Bolt head 41 either bears against the bottom side of cross-web 33 through the interposition of a washer 43 therebetween, to allow washer 9, attached pole end 7, and interposed cushion sleeve 15 to be drawn into tight registration therebetween or bears directly against the bottom side of cross-web 33 by having the diameter of central aperture 37 smaller than the diameter of bolt head 41. A plurality of radially directed ears 47 extend outward from spider 25. A downwardly extending open collar or boss 47 depends from cross-web 33.

A plurality of support legs 49 are pivotally connected at one end thereof, one to each ear 45 at a hinge pin 51 and extend outward generally equiangularly from spider 25 and terminate at ends 53. Legs 49 can be of a variety of cross-sectional configurations, one "U-shaped" configuration is shown generally at 55. Leg ends 53 includes a depending boss 57 that contains a central aperture 59 as a means for containing the fixed end 61 of a rollable caster generally shown at 63. A spring 65 is wrapped about hinge pin 51 having one end 67 bearing against central spider hub 27 and the other end 69 bearing against a rib 71 formed across leg 49 outboard of ear 45 so as to bias leg 49 and help to keep it in an upwardly folded position parallel to support pole 7 when in the storage position as shown in FIG. 2.

A means for locking and unlocking legs 49 between the support position, shown in FIG. 1, and the storage position, shown in FIG. 2, is shown generally at 73 and includes a clip 75 having a hook portion 77 at one end thereof and a trigger portion 79 at the other end thereof. Clip 75 is pivotally mounted substantially midway between hook portion 77 and trigger portion 79 at a pin 81 that spans the depending side walls 83 of leg 49. Hook portion 77 is adapted to engage collar 47 and latch leg 49 into locking support engagement with pole 7. A spring 85 is bent between trigger portion 79 and rib 71 to bias clip 75 into latching engagement with collar 47. Leg 49 is released from its locked support position by rotating or pressing trigger portion 79 against the bias pressure of spring 85 to rotate hook portion 77 out of engagement with collar 47. Leg 49 can thereafter be rotated and swung upward into storage position as shown in FIG. 2. A bevelled surface 87 is provided on the front of hook portion 77 that engages collar 47, during pivotal lowering of leg 49 from storage position to support position so that final rotation of leg 49 causes engagement of hook portion 77 into locked latching with collar 47.

What is claimed is:

1. An assembly for supporting an equipment pole having an attachment end, said assembly comprising:
    a spider having a central hub, said central hub comprising an interior surface, a portion of said interior surface defining an axial bore having an outward opening, said spider further having a plurality of radial arms extending from said central hub;
    means for attaching the equipment pole to the spider, which attaching means include a resilient sleeve defining an interior cavity and having an exterior surface, a portion of said interior cavity annularly abutting a portion of the attachment end of the equipment pole, said exterior surface annularly abutting a portion of the interior surface defined by the spider's axial bore, whereby said equipment pole may be maintained in an upright configuration extending from said axial bore;
    a plurality of support legs, each of said legs having a pivotal connection with at least one of said radial arms of said spider; and
    locking and unlocking means for locking said legs into a fixed support position and for unlocking said legs to permit rotation of said legs about said pivotal connection with said spider whereby said legs may be rotated into a storage position substantially parallel with the equipment pole.

2. The support assembly as recited in claim 1, wherein said axial bore is tapered, with the largest diameter of said bore corresponding to the outward opening of said bore, whereby said axial bore is capable of mating through the resilient sleeve with varying outer diameters of different equipment poles.

3. The support assembly as recited in claim 1, wherein the resilient sleeve comprises tapered surfaces for securing the equipment pole, whereby any of a plurality of equipment poles having different diameters may be secured in position by said tapered surfaces.

4. The support assembly as recited in claim 3, wherein the resilient sleeve comprises tapered surfaces for securing the equipment poles, whereby any of a plurality of equipment poles having different diameters may be secured in position by said tapered surfaces.

5. The support assembly as recited in claim 3, wherein said resilient sleeve includes an inserted end and a top end, and wherein the interior cavity of said sleeve is tapered, with the largest cavity diameter at the top end.

6. The support assembly as recited in claim 5, wherein the exterior surface of the sleeve is tapered, with a largest diameter of said exterior surface at the top end, and said exterior surface tapering toward the inserted end so that the smaller diameter of said sleeve mates with said axial bore of said spider by abutment of a portion of said outer surface of the sleeve against a portion of the surface defined by the axial bore.

7. The support assembly as recited in claim 2, wherein the equipment pole has a threaded bore, and said support assembly comprises a threaded bolt extending upwardly through the axial bore in the central hub, and the hub has an abutment portion, so that the head of said bolt is restrained by contact with said abutment portion, such that said spider is attached to said equipment pole by threadably mating said bolt with said threaded bore.

8. The support assembly as recited in claim 3, wherein the equipment pole has a threaded bore, and said support assembly comprises a threaded bolt extending upwardly through the axial bore in the central hub, and the hub has an abutment portion, so that the head of said bolt is restrained by contact with said abutment portion, such that said spider is attached to said equipment pole by threadably mating said bolt with said threaded bore.

9. An assembly for supporting an equipment pole having an attachment end, said assembly comprising:
    a spider having a central hub, said spider further having a plurality of radial arms extending from said central hub;
    means for attaching the attachment end of the equipment pole to the spider;
    a plurality of support legs, each of said legs having a pivotal connection with an axis passing through at least one of the radial arms of the spider, and each of said legs having at least two positions within its rotation, said at least two positions including an operational position and a storage position;

locking and unlocking means for locking said legs into a fixed support position and for unlocking said legs to permit rotation of said legs about said pivotal connection with said spider whereby said legs may be rotated into a storage position; and means for rotationally biasing the rotation of the legs about their pivotal connection, said biasing being in a rotational direction away from the locked operational position and towards the storage position.

10. The assembly as recited in claim 9 wherein said biasing means comprises a spring compressed between said leg and said spider.

11. The assembly as recited in claim 9 wherein in the storage position, each of the legs is substantially parallel to the equipment pole, and proximate thereto.

12. The assembly as recited in claim 9 wherein the legs are maintained in a storage position by force applied by said biasing means.

13. An assembly for supporting an equipment pole having an attachment end, said assembly comprising:

a spider having a central hub said spider further having a plurality of radial arms extending from said central hub;

means for attaching the attachment end of the equipment pole to the spider;

a plurality of support legs, each of said legs having a pivotal connection with an axis passing through at least one of the radial arms of the spider, and each of said legs having at least two positions within its rotation, said at least two positions including an operational position and a storage position; and locking and unlocking means for locking said legs into a fixed support position and for unlocking said legs to permit rotations of said legs about said pivotal connection with said position, said locking and unlocking means comprising a pivotally-mounted clip having a hook portion and a trigger portion whereby the locked position is maintained by a latching of the hook, and the unlocked position is attained by application of force to the trigger.

14. The assembly as recited in claim 13 wherein said spider comprises a collar extending downwardly.

15. The assembly as recited in claim 14 wherein the leg is locked into the operational position by a locking engagement of the hook with the collar.

16. The assembly as recited in claim 15 wherein the pivotally mounted clip is rotationally biased toward locking engagement.

17. The assembly as recited in claim 16 wherein said assembly comprises a spring to rotationally bias the clip toward locking engagement.

18. The assembly as recited in claim 16 wherein said hook portion comrises a beveled surface for slidable contact with the collar, said contact occurring during at least a portion of said rotation of the leg, so that the rotation of the leg toward an operational position causes first the occurrence of said slidable contact, which in turn then causes a movement of the hook about the collar, and finally causes the hook to engage the collar in the locked position.

19. An assembly for supporting an equipment pole including an attachment end having a threaded bore, said assembly comprising:

a spider having a central hub, said central hub comprising an interior surface, a portion of said interior surface defining a tapered axial bore having an outward opening, said axial bore being tapered such that the larger diameter is at said outward opening, said central hub further having a downwardly facing abutment surface on a portion of said interior surface, said spider further having a plurality of radial arms extending from said central hub, said central hub further comprising a downwardly extending annular collar;

means for attaching the equipment pole to the spider, which attaching means include a resilient sleeve defining an interior cavity and having an exterior surface, a portion of said interior cavity annularly abutting a portion of the attachment end of the equipment pole, said exterior surface annularly abutting a portion of the interior surface defined by the spider's axial bore, said attaching means further including a threaded bolt extending upwardly through the axial bore in the central hub, with the head of said bolt restrained by abutment against the abutment surface of the central hub, so that the spider is attached to the equipment pole by simultaneous mating of (1) the equipment pole with the interior cavity of the sleeve, (2) the exterior of the sleeve with the interior surface of the central hub, and (3) the threaded bolt with the threaded bore in the equipment pole, whereby said equipment pole may be maintained in an upright configuration extending from said axial bore;

a plurality of support legs, each of said legs having a pivotal connection with an axis passing through at least one of the radial arms of the spider, and each of said legs having at least two positions within its rotation, said at least two positions including an operational position and a storage position, each of said legs further comprising means for biasing the legs toward a storage position, said biasing means including a spring compressed between a portion of the leg and the spider; and locking and unlocking means for locking said legs into a fixed support position and for unlocking said legs to permit rotation of said legs about said pivotal connection with said spider, said locking and unlocking means comprising a biased, pivotally-mounted clip having a hook portion having a beveled edge and further having a trigger portion so that from an unlocked position, a locked position is accomplished by a first rotation of the leg to slidable contact between the beveled edge portion and a portion of the collar, and then by a second rotation to latch the hook over the collar, said locked position being maintained by said latching of the hook over the collar, and the unlocked position is accomplishable by application of force to the trigger.

* * * * *